United States Patent
Leavitt

(10) Patent No.: US 7,133,937 B2
(45) Date of Patent: Nov. 7, 2006

(54) INPUT DEVICES FOR ENTERING DATA INTO AN ELECTRONIC MEDICAL RECORD (EMR)

(75) Inventor: Mark Keith Leavitt, Portland, OR (US)

(73) Assignee: GE Medical Systems Information Technologies, Milwaukee, WI (US)

( * ) Notice: Subject to any disclaimer, the term of this patent is extended or adjusted under 35 U.S.C. 154(b) by 2 days.

(21) Appl. No.: 10/751,615

(22) Filed: Jan. 5, 2004

(65) Prior Publication Data

US 2004/0143689 A1    Jul. 22, 2004

Related U.S. Application Data

(63) Continuation of application No. 09/698,033, filed on Oct. 30, 2000, now abandoned.

(60) Provisional application No. 60/162,160, filed on Oct. 29, 1999.

(51) Int. Cl.
*G06F 3/00* (2006.01)
*G09G 5/00* (2006.01)

(52) U.S. Cl. .................................. 710/1; 345/179

(58) Field of Classification Search ................ 710/100, 710/2, 5; 345/169, 180; 715/700; 178/18.01
See application file for complete search history.

(56) References Cited

U.S. PATENT DOCUMENTS

| | | | | |
|---|---|---|---|---|
| 4,424,812 A * | 1/1984 | Lesnick | | 607/30 |
| 4,695,831 A * | 9/1987 | Shinn | | 345/180 |
| 4,947,261 A * | 8/1990 | Ishikawa et al. | | 358/473 |
| 4,951,079 A * | 8/1990 | Hoshino et al. | | 396/56 |
| 5,027,149 A * | 6/1991 | Hoshino et al. | | 396/56 |
| 5,051,736 A * | 9/1991 | Bennett et al. | | 345/180 |
| 5,237,647 A * | 8/1993 | Roberts et al. | | 345/419 |
| 5,608,861 A * | 3/1997 | Mead et al. | | 715/700 |
| 5,664,109 A * | 9/1997 | Johnson et al. | | 705/2 |
| 5,693,076 A * | 12/1997 | Kaemmerer | | 607/59 |
| 5,823,948 A * | 10/1998 | Ross et al. | | 600/300 |
| 5,832,450 A * | 11/1998 | Myers et al. | | 705/3 |
| 5,850,058 A * | 12/1998 | Tano et al. | | 178/18.01 |
| 5,874,947 A * | 2/1999 | Lin | | 345/169 |
| 5,892,900 A * | 4/1999 | Ginter et al. | | 726/26 |
| 6,032,119 A * | 2/2000 | Brown et al. | | 705/2 |
| 6,167,376 A * | 12/2000 | Ditzik | | 704/235 |
| 6,169,725 B1 * | 1/2001 | Gibbs et al. | | 370/216 |
| 6,218,964 B1 * | 4/2001 | Ellis | | 340/990 |
| 6,272,468 B1 * | 8/2001 | Melrose | | 705/2 |
| 6,289,316 B1 * | 9/2001 | Aghili et al. | | 705/3 |
| 6,304,848 B1 * | 10/2001 | Singer | | 705/3 |
| 6,415,256 B1 * | 7/2002 | Ditzik | | 704/231 |
| 2001/0053984 A1 * | 12/2001 | Joyce et al. | | 705/2 |
| 2002/0172498 A1 * | 11/2002 | Esenyan et al. | | 386/69 |
| 2003/0163321 A1 * | 8/2003 | Mault | | 704/270 |
| 2004/0143689 A1 * | 7/2004 | Leavitt | | 710/73 |
| 2005/0048992 A1 * | 3/2005 | Wu et al. | | 455/466 |

* cited by examiner

*Primary Examiner*—Khanh Dang
(74) *Attorney, Agent, or Firm*—Andrus Sceales Starke & Sawall, LLP

(57) ABSTRACT

A client-server based electronic medical record replaces paper records in outpatient clinics. The Internet provides physicians with the ability to use a Java-based client program to generate legible, complete notes for patient encounters that comply with HCFA guidelines. A pen-like input device for entering data into an electronic medical record is provided with one end which serves as a stylus or pointing device for being placed in contact with a touch screen and another end which has a microphone element for receiving speech signals. A microphone activation button or lever is provided to enable and disable speech recognition.

9 Claims, 4 Drawing Sheets

INPUT DEVICES FOR ENTERING DATA INTO AN ELECTRONIC MEDICAL RECORD (EMR)

CROSS REFERENCE TO RELATED APPLICATIONS

This application is a continuation of application Ser. No. 09/698,033 filed Oct. 30, 2000 now abandoned, which claims the benefit of U.S. Provisional Application Ser. No. 60/162,160 filed Oct. 29, 1999, both herein incorporated by reference.

BACKGROUND OF THE INVENTION

In order to improve healthcare for both the service provider and the recipient, it is imperative that the paper record method currently practiced be rendered obsolete by providing an electronic medical record that can be easily built and updated. In addition, with the internet playing a vastly increasing role in all of our lives, it is also imperative to utilize efficiencies that the internet provides in the healthcare environment, particularly at the point of care.

Radio took 38 years to reach 50 million listeners. Television required approximately 11 years to reach 60 million viewers. The Internet has garnered 50 million users in 5 years. Today, we are constantly reminded of the power and scale of the Internet. Without question, it is the greatest telecommunications revolution since the advent of the telephone. Its presence has created the networked economy, or the "digital economy".

The power of this newfound connectivity can precipitate productivity and efficiency gains of exponential proportions. With an unprecedented adoption curve, and generations of technical advances occurring at a breath-taking pace, the Internet has evolved from an academic medium for sharing rich research to a commercial delivery network of content, services, and workflow control.

Healthcare has endured inefficiencies, disparate legacy systems, and disjointed workflow with high latencies for many years. These difficulties are coupled with the fact that the healthcare experience has begun to deteriorate not only for the patient, but for the physician and support staff, as well.

With only an average of seven minutes of "face-to-face time" per visit, both the physician and the patient are left unfulfilled. The physician feels his/her number one priority, the quality of care, is forsaken, and the patient feels as though there is not enough time to be treated. The Internet and the digital economy can foster much needed change.

SUMMARY OF THE INVENTION

The present inventors have recognized the need for combining an electronic medical record along with an input device for entering data into the electronic medical record that permits the physician a greater degree of flexibility. Accordingly, the concept of an integrated stylus/microphone has been realized. This pen-like unit has one end which is used as a stylus and serves as a pointing device, while the other end contains a miniature microphone element which can receive speech uttered a user. A push-to-talk switch can be employed to activate speech recognition.

DETAILED DESCRIPTION OF THE PREFERRED EMBODIMENTS

The present inventors have overcome the problems presented by paper records by developing a client-server based electronic medical record (EMR) product, called Logician Enterprise (LE), designed to essentially replace the paper records in the outpatient clinic. LE allows all members of an outpatient clinic from the front desk staff to physicians to do their work efficiently with a computer-based system. If LE does not have a built in billing package, it integrates with all major Practice Management systems. In addition, LE has an interface engine allowing it to receive from transcription services, laboratory systems, and many other systems providing clinical information useful to help health care providers take on care of patients. The backend database is Oracle running on an NT Server, NetWare server, or a HPUX server (HP's version of UNIX). The preferred embodiment of the client is a Pentium 200 MHz machine with 64 MB RAM and 2 GB or larger hard disk.

In addition, in order to take advantage of the internet, a new product has been developed that leverages the Internet to deliver a set of services to ambulatory care physicians and is referred to as Logician Internet (LI). LI provides physicians with the ability to use a Java-based client program to generate legible, complete notes for patient encounters that comply with the HCFA 1997 Evaluation and Management (E&M) guidelines. Physicians use ChartRoom, a service provided on MedicaLogic.com, to store and retrieve their "charts" and view notes from anywhere. LI also utilizes the latest multi-level security technology.

Figure 1:
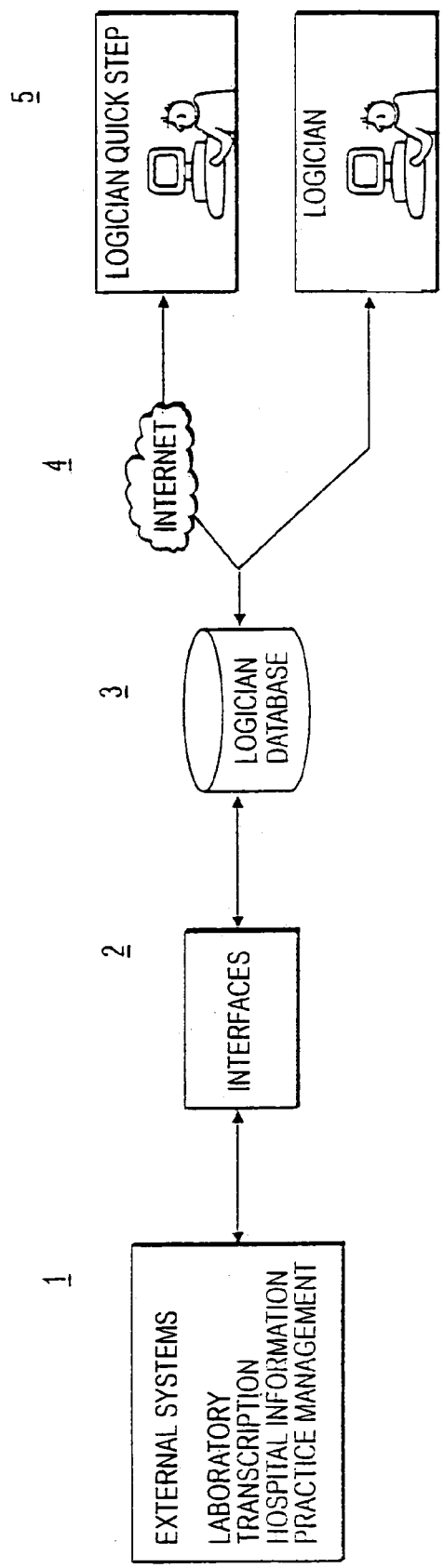
FIG. 1 illustrates an overall block diagram of an embodiment of the present invention.
Figure 2:
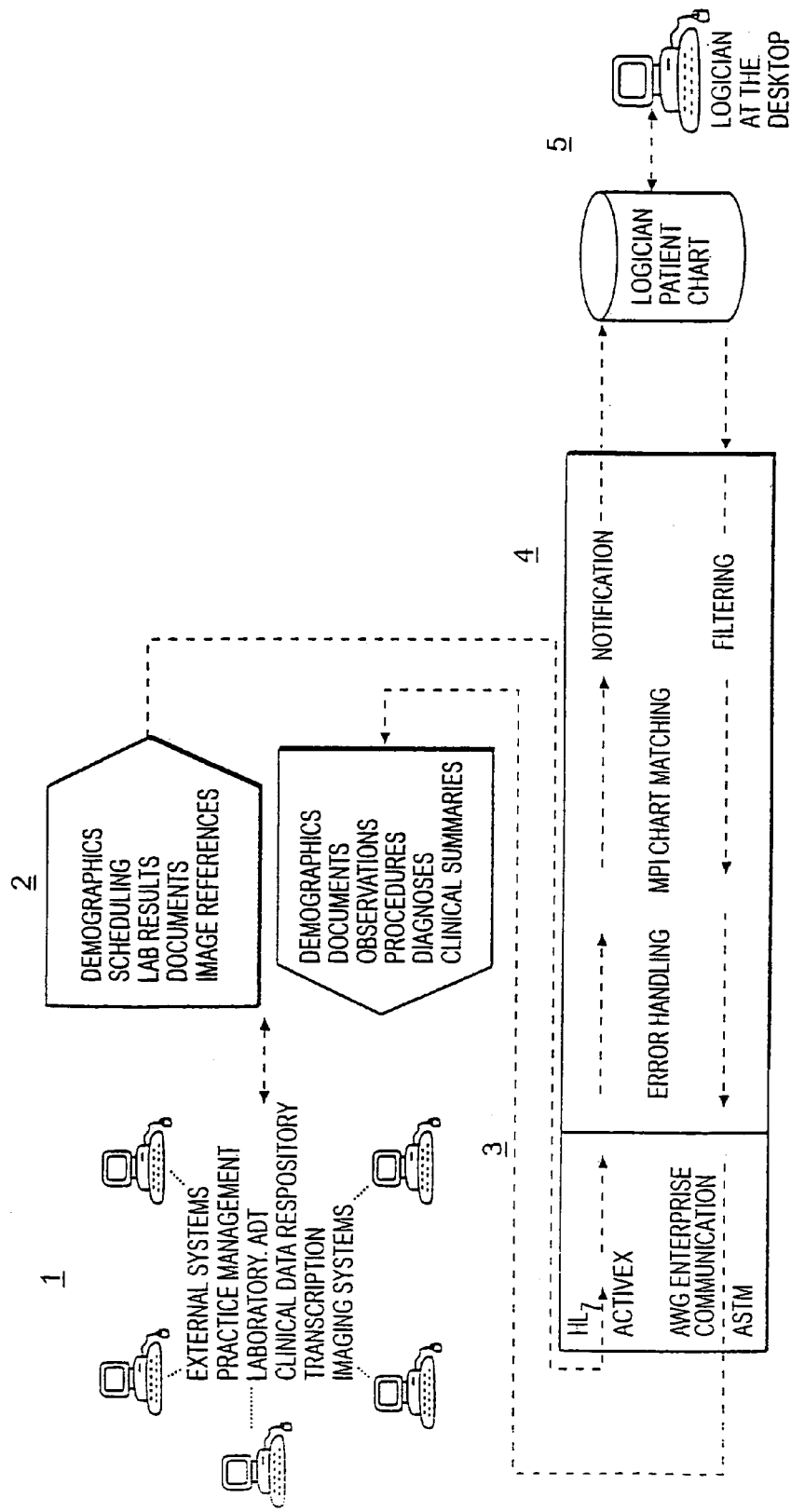
FIG. 2 illustrates a more detailed diagram of FIG. 1.

As shown in FIG. 1, external systems such as laboratory, transcription, hospital information and practice management are interconnected with a Logician database via and interfaces. The Logician database is accessed directly by a client computer or via the internet. This is shown in more detail in FIG. 2.

In addition, a web site such as, MedicaLogic.com, provides services such as by hosting KnowledgeBank which is an example of a successful effort to build community among physician users. The KnowledgeBank allows users to submit clinical forms and reports to share with other LE users. They can also download free-of-charge content to help them leverage the power of the LE product. MedicaLogic.com hosts the LI Chartroom and provides additional Web-based services to subscribers of LI such as directed links to partnered web-based clinical content that can be in the context of a specific patient.

Logician QuickStep™ combines the power of Logician with the simplicity of the Web to give physicians fast, easy access to their most important patient data (see FIG. 1). Lab results, clinical history, and clinical documents (such as transcribed reports of office visits, consultations, admissions, procedures, and discharge summaries) are immediately available over the Web.

Logician QuickStep's powerful clinical document management capabilities allow physicians to review clinical documents, add comments, and forward them to colleagues for additional action. To encourage use by physicians, Logician QuickStep was designed specifically to operate efficiently within today's paper chart workflows.

Requiring simply a Web browser and a phone line, Logician QuickStep is a secure, low-cost EMR solution that is easy to install and manage. Using interfaces MedicaLogic has already implemented with reference laboratories, hospital information systems, practice management systems, and transcription systems, Logician QuickStep offers physicians the efficiencies and decision-support benefits of EMR with little interruption to practice workflow. Unlike other Web-based clinical products, Logician QuickStep is built on Logician's powerful EMR database. As physicians require more EMR functionality, they can easily step up to Logician. All the clinical information collected using Logician QuickStep becomes part of a complete EMR and can be used to measure quality and report outcomes.

How Logician QuickStep works will now be described briefly. Lab results, transcription, and reports including consultation, radiology, and discharge summaries are electronically exchanged with Logician. Logician's data exchange engine enables information flow to and from the Logician database. Information and structured data stored in the Logician database are available for quality of care reports and outcomes analysis. Logician QuickStep allows easy web access to reported clinical information requiring physician review. Users can access patient-specific history of clinical activity from their office, home, or the hospital. Logician automates clinical workflow, enables documentation of the patient encounter, and delivers patient management tools at the point of care.

For full system and workflow integration, multiple external systems will exchange data with Logician. The rich data sets enable information flow to/from a wide variety of external information systems. Industry-standard formats and communication protocols provide efficient interfaces to other compliant systems. Accurate chart matches, robust error handling, immediate notification to clinicians, and confidentiality filtering of exported data are ensured. Through CCOW, Logician and other applications on the same client workstation always reference the same patient.

LinkLogic™, which is a name used for the internal data exchange engine, enables the efficient and intelligent sharing of data among Logician products and various external systems, including practice management, transcription, laboratory, document imaging, hospital information systems, and clinical data repositories. It supports the drive to bring information together for the benefit of physicians, patients, and the entire healthcare enterprise.

LinkLogic makes important information from sources outside the clinic (such as laboratory test results, hospital discharge summaries, transcription reports, consultation reports) available at the point of care. LinkLogic also exports the ambulatory care data that is necessary for accurate enterprise outcomes and quality reporting. It makes patient demographic information, clinical summaries, and chart notes available to the health system's clinical data repository. There, data can be analyzed in combination with patient data from other care settings, providing valuable reports on a health system's progress toward meeting quality and business performance goals.

LinkLogic exchanges the following information:

1. Lab results: With LabLink, lab values arrive directly from the reference or hospital lab and are immediately viewable from the desktop or flowsheet. Lab values that is beyond an acceptable range trigger and send an "urgent" document to the responsible physician.

2. Scheduling: With ScheduLink, appointments scheduled in a front-office practice management system appear on the Logician desktop immediately.

3. Registration: With DemographicsLink, patient information entered in a separate registration system creates or updates the patient's chart in Logician.

4. Documents: With NotesLink, transcription reports, hospital discharge summaries, radiology reports, and consultation reports are delivered to the appropriate clinician's Logician desktop as soon as they are available from external sources.

5. Clinical Observations: With ObservationsLink, clinical data gathered during patient encounters is exported directly to the hospital's clinical data repository.

6. Procedures/Diagnoses: With ProceduresLink, patient encounter information, including procedures and diagnoses, is exported to the billing or managed care system at the clinic.

7. Image References: With ImageLink, references to images stored in external document imaging systems appear in a patient's chart in Logician for easy viewing.

8. Clinical Summary Document: A summary document of the patient's clinical information can be exported to a clinical data repository.

In summary, all of the tools mentioned above enable more accurate and efficient treatment of a patient at the point of care. This should improve the physician-patient relationship by increasing the amount of information available during the patient encounter.

Input devices for entering data into the EMR that are commonly used are the keyboard and mouse. These devices are self explanatory.

Figure 3:
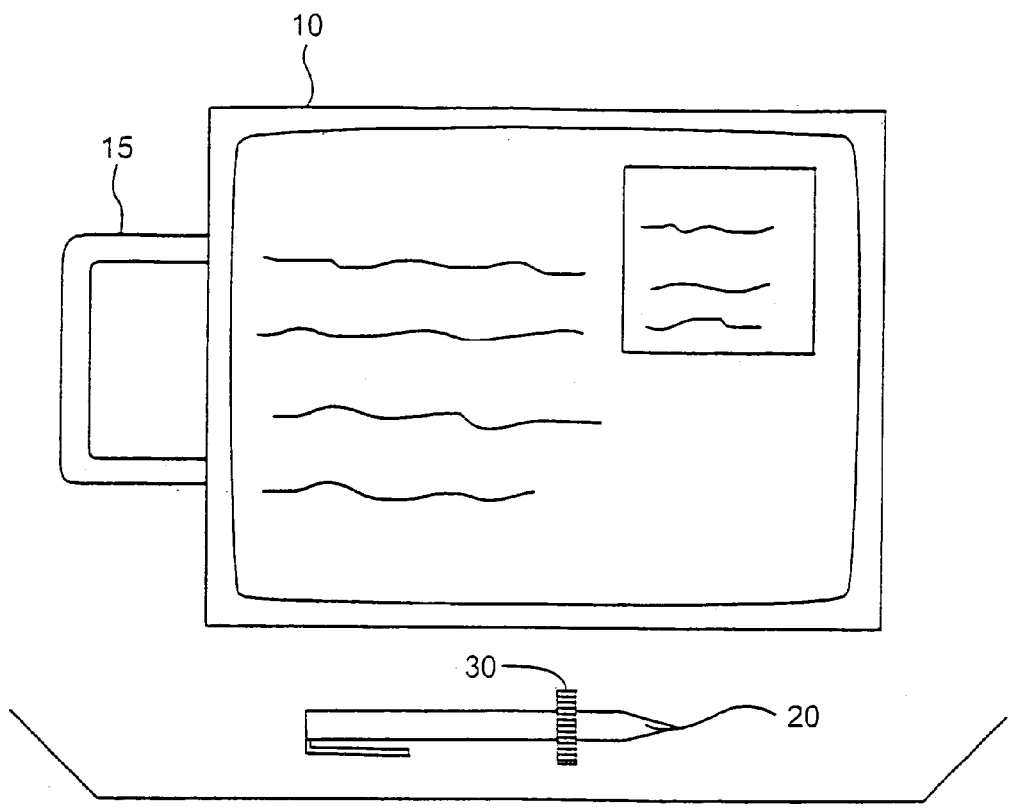
FIG. 3 illustrates a template and a pen-like input device.
Figure 4:
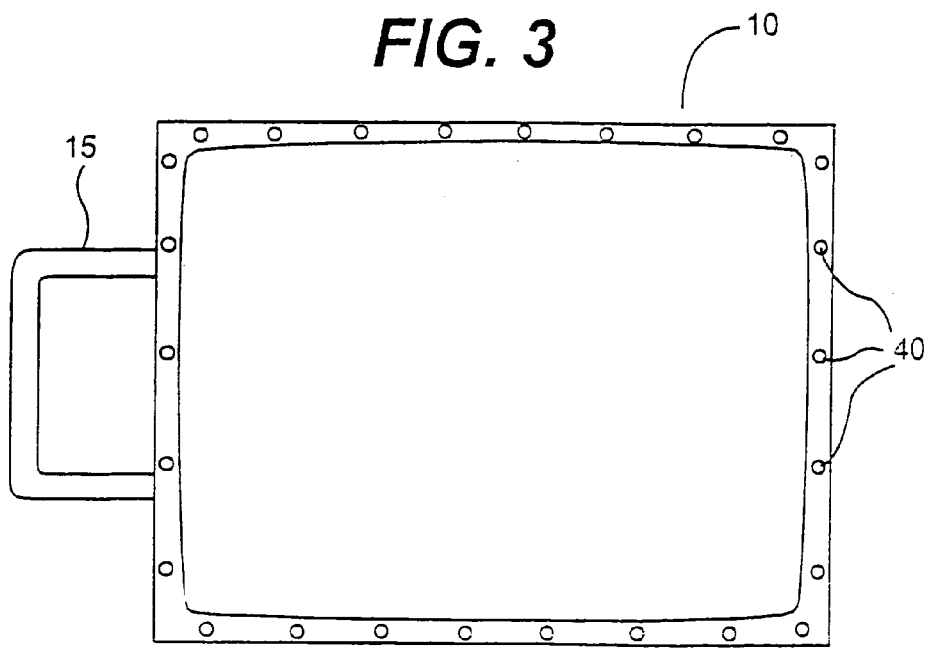
FIG. 4 illustrates another embodiment of the template including condensed microphones.

However, to permit a physician a greater degree of flexibility, it is necessary to improve upon these input devices. One option, as shown in FIG. 3, is to provide a template 10, with handle 15, having a wireless connection to a computer. The template can have a pen-like input device 20, possibly with a wireless connection. The template has voice recognition capability and the pen can be squeezed at some pressure sensitive portion such as portion 30 to act as a microphone. This way a physician can quickly and easily enter information regarding a patient without having to use a keyboard or mouse.

Alternatively, the template 10 can be provided with phased arrays comprising condensed microphones 40 surrounding the perimeter of the template which focuses sound reception toward the physician. This way the physician can speak directly into the template and not worry about the input of external noise which may cause errors in data entry.

Figure 5:
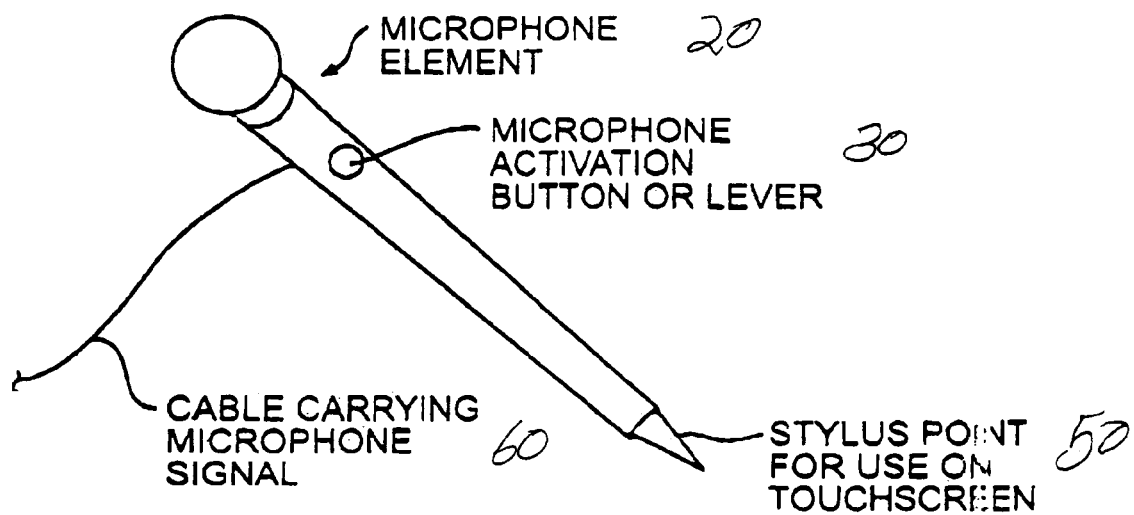
FIG. 5 illustrates an alternate embodiment of the input device.

FIG. 5 illustrates another embodiment of the microphone element. Having a microphone activation button or lever 30. A stylus point 50 can be used for contacting a touch screen. Finally, there is an optional cable 60 which carries a microphone signal.

For many applications, particularly medical applications, physicians need a way to smoothly combine two data entry modalities: (1) a navigation/selection with a "pointing device", and (2) a microphone for voice capture or speech recognition. This problem has been solved in the past by the use of a separate head-worn microphone and a mouse or other pointing device. The head-worn microphone keeps the hands free to use the mouse or other pointing device. However, a head-worn microphone is objectionable to many users, particularly physicians, because it is awkward to put on and take off for intermittent use and is likely to become entangled with other medical instruments such as stethoscopes. In addition, it is distracting during face-to-face communication with a patient. Also, if a user forgets to remove the headset and gets up to move away from the computer, it is possible to damage the microphone, the cord and plug, or even the pull the laptop computer off a desktop.

Therefore, the present inventors have designed an integrated stylus/microphone which has one end used as a stylus and another end used as a miniature microphone element to receive speech signals. Another element of the device is a push-to-talk switch, which allows speech recognition to be activated and deactivated easily without interfering with the position of a cursor in a computer application. The design of the unit is such that it is held as a pen while pointing, and with only a slight rotation of the thumb upwards, falls naturally into position as a hand-held microphone. Because the microphone is held close to the mouth, extraneous noises are minimized and the speech amplitude is maximized, which produces the best speech recognition results. The unit also has an appearance which is familiar and comfortable to both the physician and patient.

While the disclosure above has been undertaken in connection with the preferred embodiments, one of ordinary skill in the art would be enabled by this disclosure to make various modifications to the preferred embodiments and still be within the scope and spirit of the present invention.

What is claimed is:

1. A system for inputting data into an electronic medical record comprising:
   a pen-like input device with an elongated body having a first end and a second end;
   a stylus point at the first end of the pen-like input device configured to point to a touch screen;
   a microphone element at the second end of the pen-like input device for receiving speech signals from a user;
   a microphone activation button located on the elongated body, wherein the activation button is activated and deactivated to enable and disable speech recognition by the microphone element; and
   a logician database coupled with the pen-like input device such that the logician database is configured to send data to an external system from the pen-like input device, and is further configured to receive data from the external system when requested by the pen-like input device, wherein the external system includes a practice management system, a transaction system, a laboratory system, a document imaging system, a hospital information system and a clinical data repository;
   wherein fields in the electronic medical record are populated with the input data when the microphone activation button is activated, and further wherein the input data includes the speech signals collected by the microphone.

2. The pen-like input device according to claim 1, further comprising a cable which carries the microphone signal to a template which displays the data.

3. The pen-like input device according to claim 1, wherein the microphone activation button is located near the second end.

4. A computing device for manipulating an electronic medical record, comprising:
   a processor configured to receive input data for entry into the electronic medical record;
   a display configured to display the electronic medical record, wherein the display is a touch screen; and
   an input device for inputting data into an electronic medical record, the input device including:
     an elongated body having a first end and a second end;
     a stylus point at the first end configured to be used with the touch screen display;
     a microphone element at the second end for receiving speech signals from the user; and
     a microphone activation button located on the elongated body which is activated and deactivated to actuate the processor to enable and disable speech recognition by the microphone element
     wherein the processor is configured to populate an electronic medical record with input data spoken into the microphone element of the input device while the microphone activation button is activated, and
   further wherein the computing device is coupled to a logician database, the logician database configured to send data to an external system from the computing device, and is further configured to receive data from the external system to the computing device wherein the external system includes a practice management system, a transaction system, a laboratory system, a document imaging system, a hospital information system and a clinical data repository.

5. The computing device of claim 4, wherein the processor is further configured to actuate a voice recognition capability based on activation and deactivation of the microphone activation button.

6. The computing device of claim 4, wherein the microphone element is a condensed microphone.

7. An input device for inputting data into an electronic medical record through a computing device, the input device comprising:
   an elongated body having a first end and a second end;
   a stylus point at the first end which can be used to point to a touch screen;
   a microphone element at the second end for receiving input data in the form of speech signals from a user; and
   a microphone activation button located on the elongated body which is activated and deactivated to enable and disable speech recognition by the computing device based on input data received through the microphone element
   wherein fields in the electronic medical record are populated with the input data when the microphone activation button is activated, and
   further wherein the computing device is coupled to a logician database, the logician database configured to send data to an external system from the computing device, and is further configured to receive data from the external system to the computing device wherein the external system includes a practice management system, a transaction system, a laboratory system, a document imaging system, a hospital information system and a clinical data repository.

8. The input device according to claim 7, further comprising a cable which carries the microphone signal to the computing device which carries the microphone signal to the computing device which displays the data.

9. The input device according to claim 7, wherein the microphone activation button is located near the second end.

* * * * *